(12) United States Patent
Barnes

(10) Patent No.: US 6,210,353 B1
(45) Date of Patent: Apr. 3, 2001

(54) HIP BRACE

(75) Inventor: James O. Barnes, N104 W 14281 Donges Bay Rd., Germantown, WI (US) 53022

(73) Assignee: James O. Barnes, Germantown, WI (US)

( * ) Notice: Subject to any disclaimer, the term of this patent is extended or adjusted under 35 U.S.C. 154(b) by 0 days.

(21) Appl. No.: 09/305,140

(22) Filed: May 4, 1999

(51) Int. Cl.$^7$ ........................................................ A61F 5/00
(52) U.S. Cl. ............................ 602/19; 602/23; 602/60; 602/61; 602/62
(58) Field of Search .................... 128/96.1, 99.1, 128/100.1, 101.1, 102.1, 106.1, 109.1, 111.1, 112.1, 117.1; 602/13, 19, 23, 24, 60, 61, 63, 67, 68, 75; 2/455, 464, 465, 466, 456

(56) References Cited

U.S. PATENT DOCUMENTS

| | | | |
|---|---|---|---|
| 5,383,893 | * 1/1995 | Daneshvar | 606/201 |
| 5,425,702 | 6/1995 | Carn et al. | 602/62 |
| 5,572,737 | * 11/1996 | Valice | 2/465 |
| 5,779,658 | * 7/1998 | Saca | 602/61 |
| 5,830,168 | 11/1998 | Finnell et al. | 602/24 |
| 5,840,050 | 11/1998 | Lerman | 602/19 |

* cited by examiner

Primary Examiner—Kim M. Lewis
(74) Attorney, Agent, or Firm—Michael Best & Friedrich LLP

(57) ABSTRACT

A hip brace that dramatically reduces the pain and discomfort associate with hip degeneration. In one embodiment, the hip brace includes a girdle adapted to be wrapped around the user's waist, and a support member including an upper portion connected to the girdle and a lower portion adapted to provide lateral and upward support to the user's buttock. The lower portion is thicker (e.g., at least three times thicker) than said upper portion to facilitate support of the user's buttock. In order to provide additional support, the hip brace can further include a formed spring support connected to the support member. Preferably, the hip brace further includes at least two support straps connecting the lower portion with the girdle. In a preferred embodiment, the support member includes an inflatable member and an inflater connected to the inflatable member. For example, the inflatable member can include an inflatable bladder, and the inflater can include a hand pump, a conduit connecting the hand pump to the inflatable member, and a one-way valve.

10 Claims, 1 Drawing Sheet

HIP BRACE

FIELD OF THE INVENTION

The present invention generally relates to braces and supports that are attached to the human body for medical reasons, such as to alleviate pain or discomfort.

BACKGROUND OF THE INVENTION

As the average life expectancy for humans continues to climb, degeneration of the hip has been and will continue to be a major medical problem. Hip degeneration is characterized by a loosening of the ball-and-socket joint between the femur and the pelvis. When the ball on the femur separates from the socket on the pelvis, significant pain can occur.

Today, hip replacement has become a standard treatment for this medical problem. However, some individuals are not good candidates for hip replacement and/or choose to forego this operation. In these situations, it would be beneficial if there were other treatments available.

SUMMARY OF THE INVENTION

The present invention provides a hip brace that dramatically reduces the pain and discomfort associate with hip degeneration. The hip brace is designed to apply a lateral inward pressure on the side of the user's upper thigh so as to hold the femur in engagement with the pelvis to thereby reduce the likelihood or amount of separation. In addition, the hip brace is designed to apply an upward force on the user's buttocks so as to pull upward on the femur and further reducing the likelihood or amount of separation.

In one embodiment, the hip brace includes a girdle adapted to be stretched and wrapper around the user's waist, and a support member including an upper portion connected to the girdle and a lower portion adapted to provide lateral and upward support to the user's buttock. The lower portion is thicker (e.g., at least three times thicker) than said upper portion to facilitate support of the user's buttock. In order to provide additional support, the hip brace can further include a formed spring support connected to the support member. Preferably, the hip brace further includes at least two support straps connecting the lower portion with the girdle.

In a preferred embodiment, the support member includes an inflatable member and an inflater connected to the inflatable member. For example, the inflatable member can include an inflatable bladder, and the inflater can include a hand pump, a conduit connecting the hand pump to the inflatable member, and a one-way valve.

The above-described hip braces can be used to perform a novel method of supporting a user's hip joint. The method includes the steps wrapping a girdle around the user's torso, and pressing the lower portion of the support member into the user's buttock. The pressing step can include connecting two support straps between the lower portion and the girdle. When using the hip brace having the inflatable member, the pressing step comprises inflating the inflatable member. In this embodiment, the method can further include the step of reducing the pressing force created by the pressing step while the girdle is still attached to the user. For example, the reducing step can comprise deflating the inflatable member.

DETAILED DESCRIPTION

Figure 1:
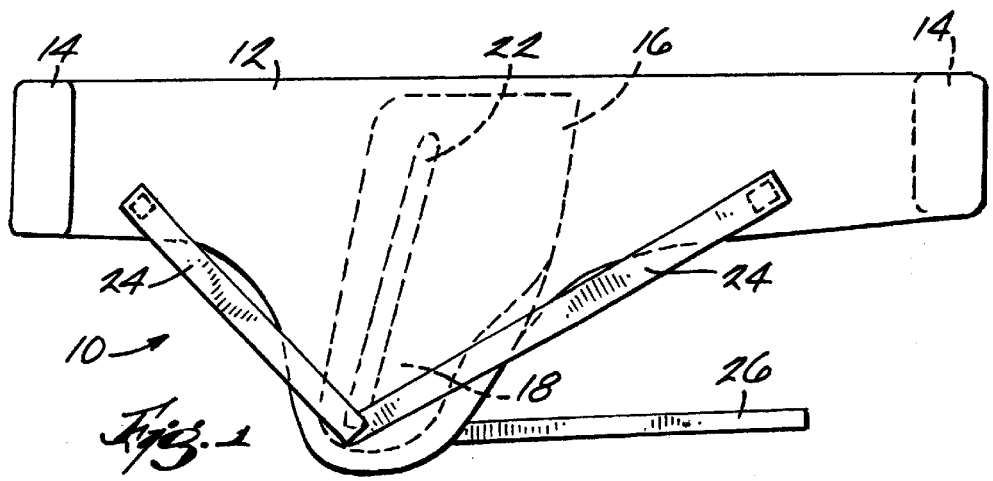
FIG. 1 illustrates a hip brace embodying the present invention.
Figure 2:
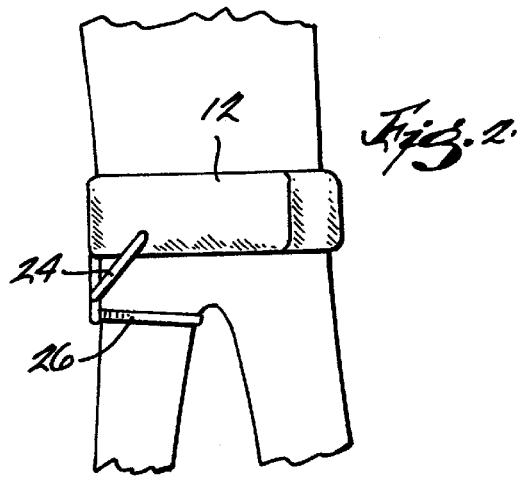
FIG. 2 is a front view of a user's mid-section with the hip brace attached to the user.
Figure 3:
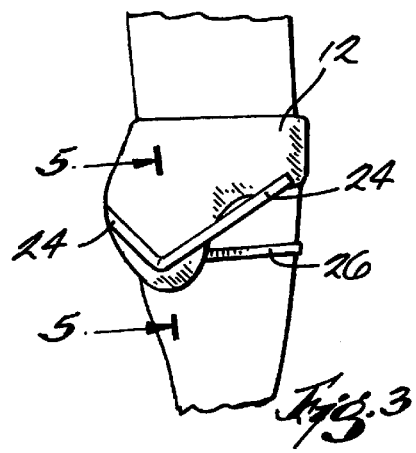
FIG. 3 is a right side view of FIG. 2.
Figure 4:
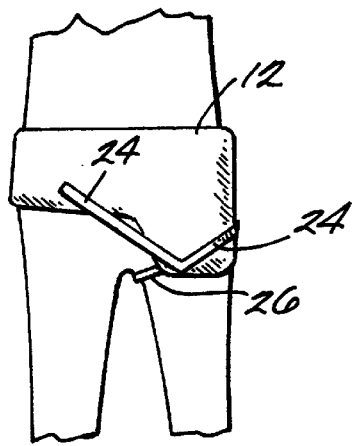
FIG. 4 is a rear view of FIG. 2.
Figure 5:
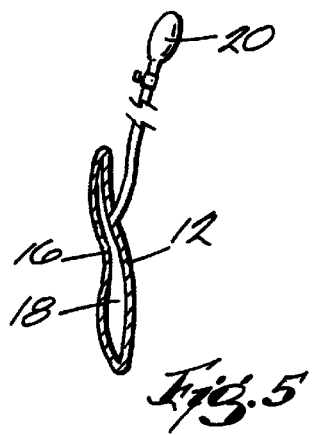
FIG. 5 is a cross section taken along line 5—5 in FIG. 3, and illustrates the use of an inflatable bladder.

The illustrated hip brace 10 includes an elastic girdle 12 that is designed to be worn around the user's waist. The girdle preferably includes an adjustable fastener 14, such as snaps, hook-and-loop fasteners, or other suitable adjustable fastener to facilitate adjustable attachment and removal from the user's body.

The hip brace 10 further includes a support member 16 secured to the girdle 12 in a location that corresponds with the user's lower hip and buttocks. The support member 16 preferably includes a relatively stiff rubber pad that is sewn into the girdle and is positioned to wrap around the user's lower hip and buttocks. The rubber pad can be formed to cup the buttocks so that pulling up on the rubber pad will provide an upward force on the buttocks. This will also prevent the hip brace 10 from creeping up as the user moves.

In order to enhance engagement with the lower buttocks, the support member 16 can include an enlarged portion 18 that is thicker than the other portions of the support member 16. The enlarged portion 18 is designed to apply pressure under the lower buttocks to further enhance the upward force applied to the buttocks. For example, the enlarged portion 18 could be formed by making the lower portion of the support member 16 thicker (e.g., 2–10 times thicker) than the other portions of the support member 16, or could be shaped as a half sphere, such as half of a tennis ball, and secured in place.

In a preferred embodiment, the support member 16 includes an inflatable bladder that can be inflated or deflated to fit the user's dimensions. The ability to inflate and deflate also makes the hip brace 10 more comfortable to the user when sitting. More specifically, the inflatable bladder can be deflated when the extra support is not needed, such as when the user is sitting or lying down. The bladder can then be re-inflated when additional support is required, such as when the user is walking. To facilitate inflation and deflation, the bladder can include an inflater in the form of a manual pump 20 with a one-way valve, similar to what is commonly used with manual blood pressure sleeves.

In order to provide extra support, a formed spring support 22 can be incorporated into the support member 16. The spring support 22 can be curved to wrap around and cup the buttocks to thereby enhance the upward force applied to the buttocks.

Two support straps 24 can be provided to hold the support member 16 in engagement with the lower buttocks. The support straps 24 can be made of any suitable material, such as elastic, cloth, or a more rigid material, such as plastic or spring steel. Preferably, the support straps 24 are adjustable so that they can be positioned in the desired position depending on the shape of the user.

A thigh strap 26 can be attached to the lower portion of the girdle 12 and wrapped around the user's thigh. The thigh strap 26 is preferably an elastic belt having an adjustable fastener (e.g., Hook-and-loop fastener, snaps, etc.) to facilitate users of different sizes. The thigh strap 26 holds the lower portion of the support member 16 in engagement with the user's buttocks. This will enhance the upward force applied to the buttocks.

The foregoing description of the present invention has been presented for purposes of illustration and description.

Furthermore, the description is not intended to limit the invention to the form disclosed herein. Consequently, variations and modifications commensurate with the above teachings, and the skill or knowledge of the relevant art, are within the scope of the present invention. The embodiments described herein are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A hip brace adapted to be worn by a user to reduce discomfort associated with hip degeneration, the hip brace comprising:
    a girdle adapted to be wrapped around the users waist, the girdle comprising an elastic material;
    a support member; and
    a formed spring support incorporated into the support member, the formed spring support further including a curve therein adapted to wrap around and cup the buttocks to thereby enhance the upward force applied to the buttocks.

2. The hip brace as claimed in claim 1, wherein the support member includes an upper portion connected to said girdle and a lower portion adapted to provide lateral and upward support to the user's buttock, wherein said lower portion is at least three times thicker than said upper portion.

3. The hip brace as claimed in claim 2, further comprising at least two support straps connecting said lower portion with said girdle.

4. A method of supporting a user's hip joint using a hip brace having a girdle and a support member in the form of an inflatable member, the method comprising the steps of:
    wrapping the girdle around the user's torso;
    positioning the inflatable member in contact with a lower portion of the user's buttock; and
    inflating the inflatable member to thereby apply pressure on the user's buttock.

5. A method as claimed in claim 4, wherein said wrapping step comprises stretching the girdle.

6. A method as claimed in claim 4 further comprising coupling two support straps between the inflatable member and the girdle.

7. A method as claimed in claim 4, further comprising the step of reducing the pressing force created by said inflating step by deflating the inflatable member to thereby increase user comfort when the user is sitting.

8. A method of supporting a user's hip joint using a hip brace having a girdle and a support member incorporating a formed spring support having a curve therein, the method comprising the steps of:
    wrapping the girdle around the user's torso; and
    positioning the formed spring support having a curve on the user, wrapping the support around the user such that it cups the buttocks to thereby enhance the upward force applied to the buttocks.

9. A method as claimed in claim 8, wherein said wrapping step comprises stretching the girdle.

10. A method as claimed in claim 8, further comprising coupling two support straps between the spring support and th girdle.

* * * * *